US006981958B1

(12) United States Patent
Gharib et al.

(10) Patent No.: US 6,981,958 B1
(45) Date of Patent: *Jan. 3, 2006

(54) IMPLANT WITH PRESSURE SENSOR FOR GLAUCOMA TREATMENT

(75) Inventors: Morteza Gharib, San Marino, CA (US); Hosheng Tu, Tustin, CA (US); Olav Bergheim, Laguna Hills, CA (US)

(73) Assignee: Glaukos Corporation, Laguna Hills, CA (US)

( * ) Notice: Subject to any disclaimer, the term of this patent is extended or adjusted under 35 U.S.C. 154(b) by 155 days.

This patent is subject to a terminal disclaimer.

(21) Appl. No.: 10/626,181

(22) Filed: Jul. 24, 2003

Related U.S. Application Data (63) Continuation of application No. 09/847,523, filed on May 2, 2001, now Pat. No. 6,666,841.

(51) Int. Cl.
*A61M 5/00* (2006.01)
*A61M 5/32* (2006.01)
(52) U.S. Cl. .......................................... 604/8; 604/175
(58) Field of Classification Search ................ 604/8, 604/175
See application file for complete search history.

(56) References Cited

U.S. PATENT DOCUMENTS

| 3,788,327 A | 1/1974 | Donowitz et al. |
| 4,037,604 A | 7/1977 | Newkirk |
| 4,168,697 A | 9/1979 | Cantekin |
| 4,175,563 A | 11/1979 | Arenberg et al. |
| 4,402,681 A | 9/1983 | Haas et al. |
| 4,428,746 A | 1/1984 | Mendez |
| 4,501,274 A | 2/1985 | Skjaerpe et al. |
| 4,521,210 A | 6/1985 | Wong |
| 4,554,918 A | 11/1985 | White |
| 4,604,087 A | 8/1986 | Joseph |
| 4,632,842 A | 12/1986 | Karwoski et al. |
| 4,634,418 A | 1/1987 | Binder |
| 4,718,907 A | 1/1988 | Karwoski et al. |
| 4,722,724 A | 2/1988 | Schocket |
| 4,733,665 A | 3/1988 | Palmaz |
| 4,750,901 A | 6/1988 | Molteno |
| 4,787,885 A | 11/1988 | Binder |
| 4,804,382 A | 2/1989 | Turina et al. |
| 4,820,626 A | 4/1989 | Williams et al. |
| 4,846,172 A | 7/1989 | Berlin |
| 4,863,457 A | 9/1989 | Lee |

(Continued)

FOREIGN PATENT DOCUMENTS

AU          200072059          12/2000

(Continued)

OTHER PUBLICATIONS

Jacobi et al., *Goniocurettage for Removing Trabecular Meshwork: Clinical Results of a New Surgical Technique in Advanced Chronic Open-Angle Glaucoma*, American Journal of Ophtoalmology, May 1999, vol. 127, No. 5, pp. 505-510.

(Continued)

*Primary Examiner*—Cheryl J. Tyler
*Assistant Examiner*—Filip Zec
(74) *Attorney, Agent, or Firm*—Knobbe Martens Olson & Bear, LLP (57) ABSTRACT

A trabecular shunt and methods for treating glaucoma are disclosed. One of the methods comprises transporting fluid from the anterior chamber of an eye to Schlemm's canal through an implant, the implant extending between the anterior chamber and Schlemm's canal; sensing an intraocular pressure using a sensor incorporated into the implant; and transmitting a signal indicative of the sensed pressure to an external receiver.

5 Claims, 10 Drawing Sheets

U.S. PATENT DOCUMENTS

| | | | |
|---|---|---|---|
| 4,886,488 A | 12/1989 | White | |
| 4,900,300 A | 2/1990 | Lee | |
| 4,936,825 A | 6/1990 | Ungerleider | |
| 4,946,436 A | 8/1990 | Smith | |
| 4,968,296 A | 11/1990 | Ritch et al. | |
| 5,041,081 A | 8/1991 | Odrich | |
| 5,073,163 A | 12/1991 | Lippman | |
| 5,092,837 A | 3/1992 | Ritch et al. | |
| 5,095,887 A | 3/1992 | Leon et al. | |
| 5,127,901 A | 7/1992 | Odrich | |
| 5,129,895 A | 7/1992 | Vassiliadis et al. | |
| 5,171,213 A | 12/1992 | Price, Jr. | |
| 5,178,604 A | 1/1993 | Baerveldt et al. | |
| 5,180,362 A | 1/1993 | Worst | |
| 5,246,451 A | 9/1993 | Trescony et al. | |
| 5,290,295 A | 3/1994 | Querals et al. | |
| 5,300,020 A | 4/1994 | L'Esperance, Jr. | |
| 5,318,513 A | 6/1994 | Leib et al. | |
| 5,334,137 A | 8/1994 | Freeman | |
| 5,338,291 A | 8/1994 | Speckman et al. | |
| 5,346,464 A | 9/1994 | Camras | |
| 5,360,399 A | 11/1994 | Stegmann | |
| 5,370,607 A | 12/1994 | Memmen | |
| 5,370,641 A | 12/1994 | O'Donnell, Jr. | |
| 5,372,577 A | 12/1994 | Ungerleider | |
| 5,397,300 A | 3/1995 | Baerveldt et al. | |
| 5,433,701 A | 7/1995 | Rubinstein | |
| 5,454,796 A | 10/1995 | Krupin | |
| 5,472,440 A | 12/1995 | Beckman | |
| 5,476,445 A | 12/1995 | Baerveldt et al. | |
| 5,486,165 A | 1/1996 | Stegmann | |
| 5,516,522 A | 5/1996 | Peyman et al. | |
| 5,520,631 A | 5/1996 | Nordquist et al. | |
| 5,557,453 A | 9/1996 | Schalz et al. | |
| 5,558,629 A | 9/1996 | Baerveldt et al. | |
| 5,558,630 A | 9/1996 | Fisher | |
| 5,562,641 A | 10/1996 | Flomenblit et al. | |
| RE35,390 E | 12/1996 | Smith | |
| 5,601,094 A | 2/1997 | Reiss | |
| 5,601,549 A | 2/1997 | Miyagi | |
| 5,626,558 A | 5/1997 | Suson | |
| 5,626,559 A | 5/1997 | Solomon | |
| 5,639,278 A | 6/1997 | Dereume et al. | |
| 5,651,783 A | 7/1997 | Reynard | |
| 5,665,114 A | 9/1997 | Weadock et al. | |
| 5,670,161 A | 9/1997 | Healy et al. | |
| 5,676,679 A | 10/1997 | Simon et al. | |
| 5,681,275 A | 10/1997 | Ahmed | |
| 5,702,414 A | 12/1997 | Richter et al. | |
| 5,702,419 A | 12/1997 | Berry et al. | |
| 5,704,907 A | 1/1998 | Nordquist et al. | |
| 5,713,844 A | 2/1998 | Peyman | |
| 5,723,005 A | 3/1998 | Herrick | |
| 5,741,333 A | 4/1998 | Frid | |
| 5,743,868 A | 4/1998 | Brown et al. | |
| 5,752,928 A | 5/1998 | de Roulhac et al. | |
| 5,766,243 A | 6/1998 | Christensen et al. | |
| 5,785,674 A | 7/1998 | Mateen | |
| 5,807,302 A | 9/1998 | Wandel | |
| 5,810,870 A | 9/1998 | Myers et al. | |
| 5,830,139 A | 11/1998 | Abreu | |
| 5,830,171 A | 11/1998 | Wallace | |
| 5,836,939 A | 11/1998 | Negus et al. | |
| 5,865,831 A | 2/1999 | Cozean et al. | |
| 5,868,697 A | 2/1999 | Richter et al. | |
| 5,879,319 A | 3/1999 | Pynson et al. | |
| 5,882,327 A | 3/1999 | Jacob | |
| 5,886,822 A | 3/1999 | Spitzer | |
| 5,893,837 A | 4/1999 | Eagles et al. | |
| 5,908,449 A | 6/1999 | Bruchman et al. | |
| 5,932,299 A | 8/1999 | Katoot | |
| 5,968,058 A | 10/1999 | Richter et al. | |
| 5,981,598 A | 11/1999 | Tatton | |
| 6,004,302 A | 12/1999 | Brierley | |
| 6,007,510 A | 12/1999 | Nigam | |
| 6,007,511 A | 12/1999 | Prywes | |
| 6,033,434 A | 3/2000 | Borghi | |
| 6,045,557 A | 4/2000 | White et al. | |
| 6,050,970 A | 4/2000 | Baerveldt | |
| 6,059,772 A | 5/2000 | Hsia et al. | |
| 6,059,812 A | 5/2000 | Clerc et al. | |
| 6,063,116 A | 5/2000 | Kelleher | |
| 6,063,396 A | 5/2000 | Kelleher | |
| 6,071,286 A | 6/2000 | Mawad | |
| 6,077,299 A | 6/2000 | Adelberg et al. | |
| 6,102,045 A | 8/2000 | Nordquist et al. | |
| 6,142,990 A | 11/2000 | Burk | |
| 6,165,210 A | 12/2000 | Lau et al. | |
| 6,168,575 B1 | 1/2001 | Soltanpour | |
| 6,174,305 B1 | 1/2001 | Mikus et al. | |
| 6,187,016 B1 | 2/2001 | Hedges et al. | |
| 6,193,656 B1 | 2/2001 | Jeffries et al. | |
| 6,197,056 B1 | 3/2001 | Schachar | |
| 6,203,513 B1 | 3/2001 | Yaron et al. | |
| 6,228,873 B1 | 5/2001 | Brandt et al. | |
| 6,231,597 B1 | 5/2001 | Deem et al. | |
| 6,241,721 B1 | 6/2001 | Cozean et al. | |
| 6,254,612 B1 | 7/2001 | Hieshima | |
| 6,266,182 B1 | 7/2001 | Morita | |
| 6,268,398 B1 | 7/2001 | Ghosh et al. | |
| 6,342,058 B1 | 1/2002 | Portney | |
| 6,375,642 B1 | 4/2002 | Grieshaber et al. | |
| 6,428,501 B1 | 8/2002 | Reynard | |
| 6,450,984 B1 | 9/2002 | Lynch et al. | |
| 6,464,724 B1 | 10/2002 | Lynch et al. | |
| 6,533,768 B1 | 3/2003 | Hill | |
| 6,544,249 B1 | 4/2003 | Yu et al. | |
| 6,585,680 B2 | 7/2003 | Bugge | |
| 6,629,981 B2 | 10/2003 | Bui et al. | |
| 6,666,841 B2 * | 12/2003 | Gharib et al. .................. 604/8 |
| 2002/0013546 A1 | 1/2002 | Grieshaber et al. | |
| 2002/0026200 A1 | 2/2002 | Savage | |
| 2002/0072673 A1 | 6/2002 | Yamamoto et al. | |
| 2002/0099434 A1 | 7/2002 | Buscemi et al. | |
| 2003/0069637 A1 | 4/2003 | Lynch et al. | |

FOREIGN PATENT DOCUMENTS

| | | |
|---|---|---|
| CA | 2244646 | 8/1998 |
| DE | 198 40 047 | 2/1998 |
| EP | 0 858 788 | 8/1998 |
| EP | 0 898 947 | 3/1999 |
| EP | 1 114 627 | 11/2001 |
| FR | 2 710 269 | 9/1993 |
| GB | 2 296 663 | 3/1995 |
| JP | 11-123205 | 5/1999 |
| WO | WO 89/00869 | 2/1989 |
| WO | WO 91/18569 | 12/1991 |
| WO | WO 92/19294 | 11/1992 |
| WO | WO 94/13234 | 6/1994 |
| WO | WO 94/21205 | 9/1994 |
| WO | WO 95/08310 | 3/1995 |
| WO | WO 98/30181 | 7/1998 |
| WO | WO 98/35639 | 8/1998 |
| WO | WO 99/26567 | 6/1999 |
| WO | WO 99/30641 | 6/1999 |
| WO | WO 99/38470 | 8/1999 |
| WO | WO 00/13627 | 3/2000 |
| WO | QO 00/64389 | 11/2000 |
| WO | WO 00/64390 | 11/2000 |
| WO | WO 00/64391 | 11/2000 |
| WO | WO 00/64393 | 11/2000 |
| WO | WO 00/72788 | 12/2000 |
| WO | WO/01/50943 | 7/2001 |

| | | |
|---|---|---|
| WO | WO 01/78631 | 10/2001 |
| WO | WO 01/78656 | 10/2001 |
| WO | WO 03/015659 | 2/2003 |

OTHER PUBLICATIONS

Jacobi et al., *Bimanual Trabecular Aspiration in Pseudoexfoliation Glaucoma: An Alternative in Nonfiltering Glaucoma Surgery*, American Journal of Opthalmology, May 1998, vol. 105, No. 5, pp. 886-894.

Jacobi et al., *Microendoscopic Travecular Surgery in Glaucoma Management*, American Journal of Ophtaolmology, Mar. 1999, vol. 106, No. 3, pp. 538-544.

Schwartz et al., *Trabecular Surgery*, Arch. Ophthalmol, Aug. 1974, vol. 92, pp. 134-138.

Hill et al., *Free-Electron Laser (FEL) Ablation of Ocular Tissues*, Lasers Med Sci, 1998, vol. 13, pp. 219-226.

Luntz et., *Travecuiotomy AB Externo and Trabeculectomy in Congenital and Adult-Onset Glaucoma*, American Journal of Ophthalmology, Feb. 1977, vol. 83, No. 2, pp. 174-179.

W. M. Grant, *Further Studies on Facility of Flow Through the Trabecular Meshwork*, AMA Archives of Ophthalmology, Oct. 1958, vol. 60, pp. 523-533.

Hill et al., *Laser Trabecular Ablation (LTA)*, Lasers in Surgery and Medicine, 1991, vol, 11, pp. 341-346.

Spiegel et al., *Schlemm's Canal Implant: A New Method to Lower Intraocular Pressure in Patients With POAG?*, Ophthalmic Surgery and Lasers, Jun. 1999, vol. 30, No. 6, pp. 492-494.

L.J. Katz, *A Call for Innovative Operations for Glaucoma*, Arch. Ophthalmol, Mar. 2000, vol. 118, pp. 412-413.

Detlev Spiegel, *Benefits and Risks of Ophthalmological Therapy: 7 Surgical Glaucoma Therapy*, Main Presentations at the XXXIII Continuing Education for Ophthalmologists in Essen (Germany), published Dec. 1998.

Hoerauf et al., *Slit-lamp-adapted optical coherence tomography of the anterior segment*, Graefe's Arch Clin Exp Ophthalmol (2000), vol. 237, pp. 8-18.

Radhakrishnan et al., *Real-Time Optical Coherence Tomography of the Anterior Segment at 1310 nm*, Arch Ophthalmol, Aug. 2002, vol. 119, pp. 1179-1185.

Grierson et al., *Age-related Changes in the Canal of Schlemm*, Eye Res. (1984) vol. 39, pp. 505-512.

Putney et al., *Intracellular Cl regulates Na-K-Cl cotransport activity in human trabecular meshwork cells*, American Journal of Physiology, Sep. 1999, vol. 277, pp. C373-383.

K. Strange, *Cellular and Molecular Physiology of Cell Volume Regulation*, CTC Press, Inc: 1994, pp. 311-321.

Tatton et al., *Maintaining Mitochondrial Membrane Impermeability: An opportunity for New Therapy in Glaucoma?*, Survey of Ophthalmology May 2001, vol. 45, Supplement 3, pp. S277-283.

R.W. Nickells, *Apoptosis of Retinal Ganglion Cells in Glaucoma: An Update of the Molecular Pathways Invovled in Cell Death*, Survey of Ophthalmology Jun. 1999, vol. 43, Supplement 1, pp. S151-161.

J.W. Rohen, *Anatomy of the aqueous outflow channels*, Glaucoma: vol. 1, Grune & Stratton: 1986. pp. 277-296.

Matsumoto et al., *Trabecular Meshwork Phagocytosis in Glaucomatous Eyes*, Ophthalmologica 1997, vol. 211, pp. 147-152.

M. B. Shields, *Study Guide for Glaucoma*, Williams & Wilkins: 1982, pp. 6-43.

Johnstone et al., *Cylindrical Tubular Structures Spanning from Trabecular Meshwork Across SC: Laboratory Studies With SEM, TEM & Tracers Correlated with Clinical Findings*, Abstract Paper No. 18. p. 39 from American Glaucoma Society 12th Annual Meeting.

W.G. Tatton, *Apoptotic mechanisms in neurodegeneration: Possible relevance to glaucoma*, European Journal of Ophthalmology 1999, vol. 9, Supplement 1, pp. S22-29.

U.S. Appl. No. 09/452,963, filed Dec. 2, 1999. Title: Expandable/Retractable Stent For Venous and Valvular Annulus Use.

* cited by examiner

IMPLANT WITH PRESSURE SENSOR FOR GLAUCOMA TREATMENT

CROSS-REFERENCE TO RELATED APPLICATION

This application is a continuation application of U.S. patent application Ser. No. 09/847,523, filed May 2, 2001 now U.S. Pat. No. 6,666,841, and entitled "Bifurcatable Trabecular Shunt for Glaucoma Treatment," the entirety of which is hereby incorporated by reference.

BACKGROUND OF THE INVENTION

The present invention generally relates to medical devices and methods for reducing intraocular pressure in the animal eye. More particularly, the present invention relates to the treatment of glaucoma by permitting aqueous humor to flow out of the anterior chamber through a surgically implanted pathway.

The human eye is a specialized sensory organ capable of light reception and able to receive visual images. The trabecular meshwork serves as a drainage channel and is located in anterior chamber angle formed between the iris and the cornea. The trabecular meshwork maintains a balanced pressure in the anterior chamber of the eye by draining aqueous humor from the anterior chamber.

About two percent of people in the United States have glaucoma. Glaucoma is a group of eye diseases encompassing a broad spectrum of clinical presentations, etiologies, and treatment modalities. Glaucoma causes pathological changes in the optic nerve, visible on the optic disk, and it causes corresponding visual field loss, resulting in blindness if untreated. Lowering intraocular pressure is the major treatment goal in all glaucomas.

In glaucomas associated with an elevation in eye pressure (intraocular hypertension), the source of resistance to outflow is mainly in the trabecular meshwork. The tissue of the trabecular meshwork allows the aqueous humor ("aqueous") to enter Schlemm's canal, which then empties into aqueous collector channels in the posterior wall of Schlemm's canal and then into aqueous veins, which form the episcleral venous system. Aqueous humor is a transparent liquid that fills the region between the cornea, at the front of the eye, and the lens. The aqueous humor is continuously secreted by the ciliary body around the lens, so there is a constant flow of aqueous humor from the ciliary body to the eye's front chamber. The eye's pressure is determined by a balance between the production of aqueous and its exit through the trabecular meshwork (major route) or uveal scleral outflow (minor route). The trabecular meshwork is located between the outer rim of the iris and the back of the cornea, in the anterior chamber angle. The portion of the trabecular meshwork adjacent to Schlemm's canal (the juxtacanilicular meshwork) causes most of the resistance to aqueous outflow.

Glaucoma is grossly classified into two categories: closed-angle glaucoma, also known as angle closure glaucoma, and open-angle glaucoma. Closed-angle glaucoma is caused by closure of the anterior chamber angle by contact between the iris and the inner surface of the trabecular meshwork. Closure of this anatomical angle prevents normal drainage of aqueous humor from the anterior chamber of the eye. Open-angle glaucoma is any glaucoma in which the angle of the anterior chamber remains open, but the exit of aqueous through the trabecular meshwork is diminished. The exact cause for diminished filtration is unknown for most cases of open-angle glaucoma. Primary open-angle glaucoma is the most common of the glaucomas, and it is often asymptomatic in the early to moderately advanced stage. Patients may suffer substantial, irreversible vision loss prior to diagnosis and treatment. However, there are secondary open-angle glaucomas which may include edema or swelling of the trabecular spaces (e.g., from corticosteroid use), abnormal pigment dispersion, or diseases such as hyperthyroidism that produce vascular congestion.

All current therapies for glaucoma are directed at decreasing intraocular pressure. Medical therapy includes topical ophthalmic drops or oral medications that reduce the production or increase the outflow of aqueous. However, these drug therapies for glaucoma are sometimes associated with significant side effects, such as headache, blurred vision, allergic reactions, death from cardiopulmonary complications, and potential interactions with other drugs. When drug therapy fails, surgical therapy is used. Surgical therapy for open-angle glaucoma consists of laser trabeculoplasty, trabeculectomy, and implantation of aqueous shunts after failure of trabeculectomy or if trabeculectomy is unlikely to succeed. Trabeculectomy is a major surgery that is widely used and is augmented with topically applied anticancer drugs, such as 5-flurouracil or mitomycin-C to decrease scarring and increase the likelihood of surgical success.

Approximately 100,000 trabeculectomies are performed on Medicare-age patients per year in the United States. This number would likely increase if the morbidity associated with trabeculectomy could be decreased. The current morbidity associated with trabeculectomy consists of failure (10–15%); infection (a life long risk of 2–5%); choroidal hemorrhage, a severe internal hemorrhage from low intraocular pressure, resulting in visual loss (1%); cataract formation; and hypotony maculopathy (potentially reversible visual loss from low intraocular pressure).

For these reasons, surgeons have tried for decades to develop a workable surgery for the trabecular meshwork.

The surgical techniques that have been tried and practiced are goniotomy/trabeculotomy and other mechanical disruptions of the trabecular meshwork, such as trabeculopuncture, goniophotoablation, laser trabecular ablation, and goniocurretage. These are all major operations and are briefly described below.

Goniotomy/Trabeculotomy: Goniotomy and trabeculotomy are simple and directed techniques of microsurgical dissection with mechanical disruption of the trabecular meshwork. These initially had early favorable responses in the treatment of open-angle glaucoma. However, long-term review of surgical results showed only limited success in adults. In retrospect, these procedures probably failed due to cellular repair and fibrosis mechanisms and a process of "filling in." Filling in is a detrimental effect of collapsing and closing in of the created opening in the trabecular meshwork. Once the created openings close, the pressure builds back up and the surgery fails.

Trabeculopuncture. Q-switched Neodynium (Nd) YAG lasers also have been investigated as an optically invasive technique for creating full-thickness holes in trabecular meshwork. However, the relatively small hole created by this trabeculopuncture technique exhibits a filling-in effect and fails.

Goniophotoablation/Laser Trabecular Ablation: Goniophotoablation is disclosed by Berlin in U.S. Pat. No. 4,846,172 and involves the use of an excimer laser to treat glaucoma by ablating the trabecular meshwork. Additionally, an Erbium:YAG laser was used to create full-thickness holes through trabecular meshwork in a primate model and a limited human clinical trial at the University of California, Irvine. (Hill et al., Lasers in Surgery and Medicine 11:341–346, 1991). Although morbidity was zero in both trials, success rates did not warrant further human trials. Failure was again from filling in of surgically created defects in the trabecular meshwork by repair mechanisms.

Goniocurretage: This is an ab interno (from the inside), mechanically disruptive technique that uses an instrument similar to a cyclodialysis spatula with a microcurrette at the tip. Initial results were similar to trabeculotomy: it failed due to repair mechanisms and a process of filling in.

Although trabeculectomy is the most commonly performed filtering surgery, viscocanulostomy (VC) and non-penetrating trabeculectomy (NPT) are two new variations of filtering surgery. These are ab externo (from the outside), major ocular procedures in which Schlemm's canal is surgically exposed by making a large and very deep scleral flap. In the VC procedure, Schlemm's canal is cannulated and viscoelastic substance injected (which dilates Schlemm's canal and the aqueous collector channels). In the NPT procedure, the inner wall of Schlemm's canal is stripped off after surgically exposing the canal.

Trabeculectomy, VC, and NPT involve the formation of an opening or hole under the conjunctiva and scleral flap into the anterior chamber, such that aqueous humor is drained onto the surface of the eye or into the tissues located within the lateral wall of the eye. These surgical operations are major procedures with significant ocular morbidity. When trabeculectomy, VC, and NPT are thought to have a low chance for success, a number of implantable drainage devices have been used to ensure that the desired filtration and outflow of aqueous humor through the surgical opening will continue. The risk of placing a glaucoma drainage device also includes hemorrhage, infection, and diplopia (double vision).

Examples of implantable shunts and surgical methods for maintaining an opening for the release of aqueous humor from the anterior chamber of the eye to the sclera or space beneath the conjunctiva have been disclosed in, for example, U.S. Pat. No. 6,059,772 to Hsia et al., and No. 6,050,970 to Baerveldt.

All of the above embodiments and variations thereof have numerous disadvantages and moderate success rates. They involve substantial trauma to the eye and require great surgical skill in creating a hole through the full thickness of the sclera into the subconjunctival space. The procedures are generally performed in an operating room and have a prolonged recovery time for vision.

The complications of existing filtration surgery have prompted ophthalmic surgeons to find other approaches to lowering intraocular pressure.

The trabecular meshwork and juxtacanilicular tissue together provide the majority of resistance to the outflow of aqueous and, as such, are logical targets for surgical removal in the treatment of open-angle glaucoma. In addition, minimal amounts of tissue are altered and existing physiologic outflow pathways are utilized.

As reported in Arch. Ophthalm. (2000) 118:412, glaucoma remains a leading cause of blindness, and filtration surgery remains an effective, important option in controlling the disease. However, modifying existing filtering surgery techniques in any profound way to increase their effectiveness appears to have reached a dead end. The article further states that the time has come to search for new surgical approaches that may provide better and safer care for patients with glaucoma.

Therefore, there is a great clinical need for the treatment of glaucoma by a method that is faster, safer, and less expensive than currently available modalities.

SUMMARY OF THE INVENTION

Glaucoma surgical morbidity would greatly decrease if one were to bypass the focal resistance to outflow of aqueous only at the point of resistance, and to utilize remaining, healthy aqueous outflow mechanisms. This is in part because episcleral aqueous humor exerts a backpressure that prevents intraocular pressure from going too low, and one could thereby avoid hypotony. Thus, such a surgery would virtually eliminate the risk of hypotony-related maculopathy and choroidal hemorrhage. Furthermore, visual recovery would be very rapid, and the risk of infection would be very small, reflecting a reduction in incidence from 2–5% to about 0.05%.

Techniques performed in accordance with the aspects of the invention may be referred to generally as "trabecular bypass surgery." Advantages of this surgery include lowering intraocular pressure in a manner which is simple, effective, disease site-specific, and can potentially be performed on an outpatient basis.

Trabecular bypass surgery (TBS) creates an opening, a slit, or a hole through trabecular meshwork with minor microsurgery. TBS has the advantage of a much lower risk of choroidal hemorrhage and infection than prior techniques, and it uses existing physiologic outflow mechanisms. In some aspects, this surgery can potentially be performed under topical or local anesthesia on an outpatient basis with rapid visual recovery. To prevent "filling in" of the hole, a biocompatible elongated device is placed within the hole and serves as a stent. U.S. patent application Ser. No. 09/549,350, filed Apr. 14, 2000, the entire contents of which are incorporated herein by reference, discloses trabecular bypass surgery.

In accordance with some embodiments, a trabecular shunt for transporting aqueous humor is provided. The trabecular shunt includes a hollow, elongate tubular element, having an inlet section and an outlet section. The outlet section includes two bifurcatable segments or elements, adapted to be positioned and stabilized inside Schlemm's canal.

In one aspect, the trabecular shunt is placed inside a delivery apparatus. When the trabecular shunt is deployed from the delivery apparatus into the eye, the two bifurcatable elements of the outlet section bifurcate in substantially opposite directions. In one embodiment, a deployment mechanism within the delivery apparatus includes a push-pull type plunger.

In another aspect, a delivery applicator may be placed inside a lumen of the hollow, elongate tube of the trabecular shunt. The delivery applicator may include a deployment mechanism for causing the two bifurcatable elements of the outlet section to bifurcate. In some embodiments, the delivery applicator may be a guidewire, an expandable basket, an inflatable balloon, or the like.

In accordance with another feature, at least one of the two bifurcatable elements is made of a shape-memory material, such as Nitinol or a shape-memory plastic. The shape-memory material has a preshape and a shape-transition temperature, such that the shape-memory trabecular shunt bifurcates to its preshape when it is heated to above the shape-transition temperature. The preshape of the two bifurcatable elements material may be at an angle with respect to the inlet section, preferably between about 70 degrees and about 110 degrees. An external heat source may be provided, which is adapted for heating the shape-memory material to above the shape-transition temperature of the shape-memory material.

In some aspects, the trabecular shunt may be made of one or more of the following materials: polyvinyl alcohol, polyvinyl pyrolidone, collagen, heparinized collagen, polytetrafluoroethylene, expanded polytetrafluoroethylene, fluorinated polymer, fluorinated elastomer, flexible fused silica, polyolefin, polyester, polyimide, polysilison, silicone, polyurethane, Nylon™, polypropylene, hydroxyapetite, precious metal, Nitinol, stainless steel, biodegradable materials, and biocompatible materials. Further, the outlet section of the trabecular shunt may be configured as a coil, mesh, spiral, or other appropriate configuration as will apparent to those of skill in the art. Further, the outlet section of the trabecular shunt may be porous, semi-permeable, fishbone, and/or of a continuous, solid form. The outlet section of the trabecular shunt may have a cross-sectional shape that is elliptical (e.g., oval), round, circular, D-shape, semi-circular, or irregular (asymmetrical) shape.

In one embodiment, at least one of the two bifurcatable elements has a tapered distal end, adapted for insertion ease. The trabecular shunt may have its surface coated with a coating material selected from one or more of the following: polytetrafluoroethylene (e.g., Teflon™), polyimide, hydrogel, heparin, hydrophilic compound, anti-angiogenic factor, anti-proliferative factor, therapeutic drugs, and the like. The surface coating material may also provide a mechanism for site-specific therapies.

In one embodiment, the device may include a flow-restricting member for restricting at least one component in fluid. The flow-restricting member may be a filter comprising one or more filtration materials selected from the following: expanded polytetrafluoroethylene, cellulose, ceramic, glass, Nylon, plastic, fluorinated material, or the like. The flow-restricting member may advantageously be a filter selected from the following group of filter types: hydrophobic, hydrophilic, membrane, microporous, and non-woven. The flow-restricting member acts to limit or prevent the reflux of any undesired component or contaminant of blood, such as red blood cells or serum protein, from the aqueous veins into the anterior chamber. It is useful to restrict one or more of the following components or contaminants: platelets, red blood cells, white blood cells, viruses, bacteria, antigens, and toxins.

The trabecular shunt may include a pressure sensor for measuring the pressure of the anterior chamber of an eye of a patient. The pressure sensor may further include an electromagnetic (e.g., radiofrequency) transmitter, for wirelessly transmitting pressure measurements to a pressure receiver outside the patient's body.

Among the advantages of trabecular bypass surgery is its simplicity. The microsurgery may potentially be performed on an outpatient basis with rapid visual recovery and greatly decreased morbidity. There is a lower risk of infection and choroidal hemorrhage, and there is a faster recovery, than with previous techniques.

Further features and advantages of the invention will become apparent to one of skill in the art in view of the Detailed Description that follows, when considered together with the attached drawings and claims.

DETAILED DESCRIPTION OF EXEMPLARY EMBODIMENTS

FIGS. 1 to 8 illustrate an apparatus for the treatment of glaucoma by trabecular bypass surgery.

Figure 1:
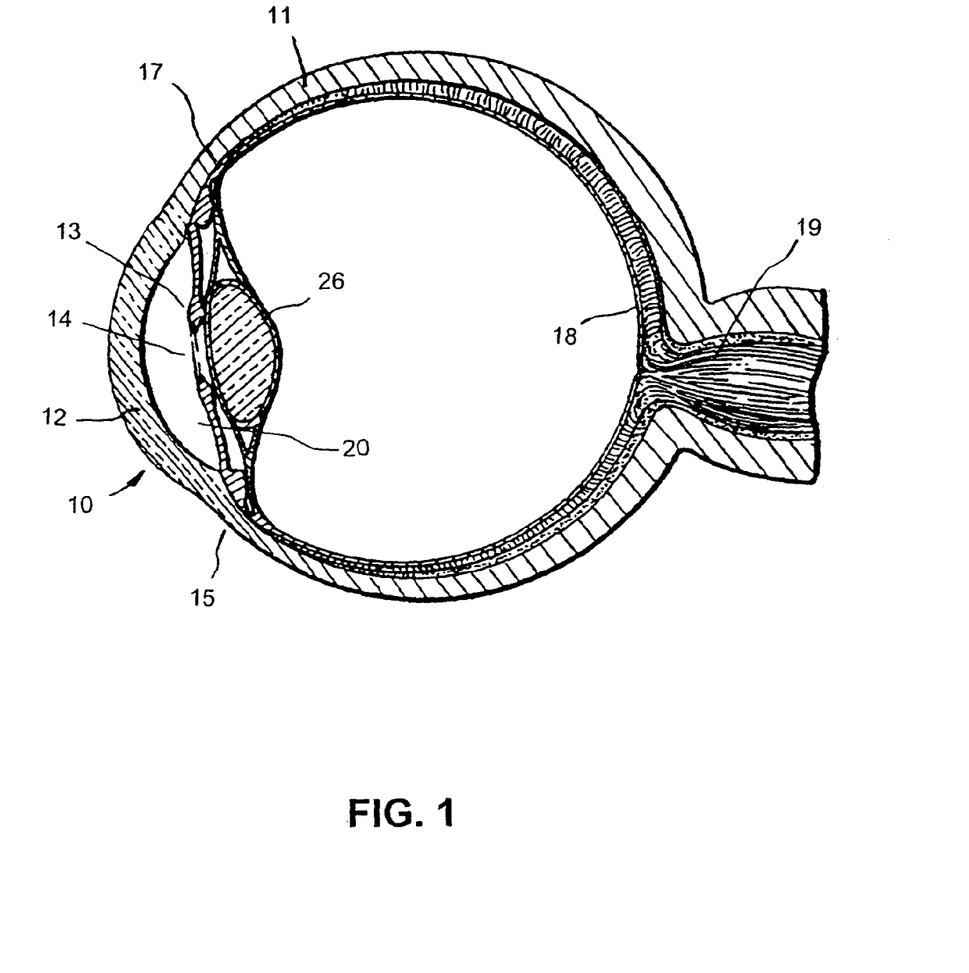
FIG. 1 is a sagittal sectional view of an eye.
Figure 2:
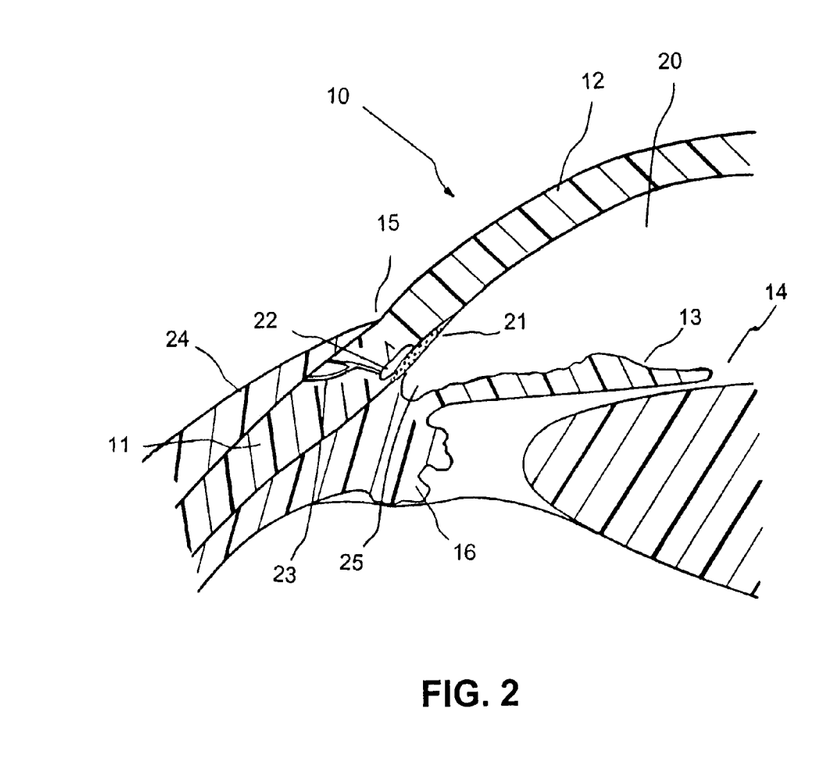
FIG. 2 is a cross-sectional view of the anterior chamber of an eye.

FIG. 1 is a sagittal sectional view of an eye 10, while FIG. 2 is a close-up view, showing the relative anatomical locations of trabecular meshwork 21, the anterior chamber 20, and Schlemm's canal 22. Thick collagenous tissue known as sclera 11 covers the entire eye 10 except that portion covered by the cornea 12. The cornea 12 is a thin transparent tissue that focuses and transmits light into the eye and through the pupil 14, which is the circular hole in the center of the iris 13 (colored portion of the eye). The cornea 12 merges into the sclera 11 at a juncture referred to as the limbus 15. The ciliary body 16 extends along the interior of the sclera 11 and is coextensive with the choroid 17. The choroid 17 is a vascular layer of the eye 10, located between the sclera 11 and retina 18. The optic nerve 19 transmits visual information to the brain and is the anatomic structure that is progressively destroyed by glaucoma.

The anterior chamber 20 of the eye 10, which is bound anteriorly by the cornea 12 and posteriorly by the iris 13 and lens 26, is filled with aqueous humor ("aqueous"). Aqueous is produced primarily by the ciliary body 16, then moves anteriorly through the pupil 14 and reaches the anterior chamber angle 25, formed between the iris 13 and the cornea 12. In a normal eye, the aqueous is removed from the anterior chamber 20 through the trabecular meshwork 21. Aqueous passes through trabecular meshwork 21 into Schlemm's canal 22 and thereafter through the aqueous veins 23, which merge with blood-carrying veins and into the systemic venous circulation. Intraocular pressure is maintained by the intricate balance between secretion and outflow of the aqueous in the manner described above. Glaucoma is, in most cases, characterized by the excessive buildup of aqueous humor in the anterior chamber 20, which leads to an increase in intraocular pressure. Fluids are relatively incompressible, and pressure is directed relatively equally throughout the eye.

Figure 8:
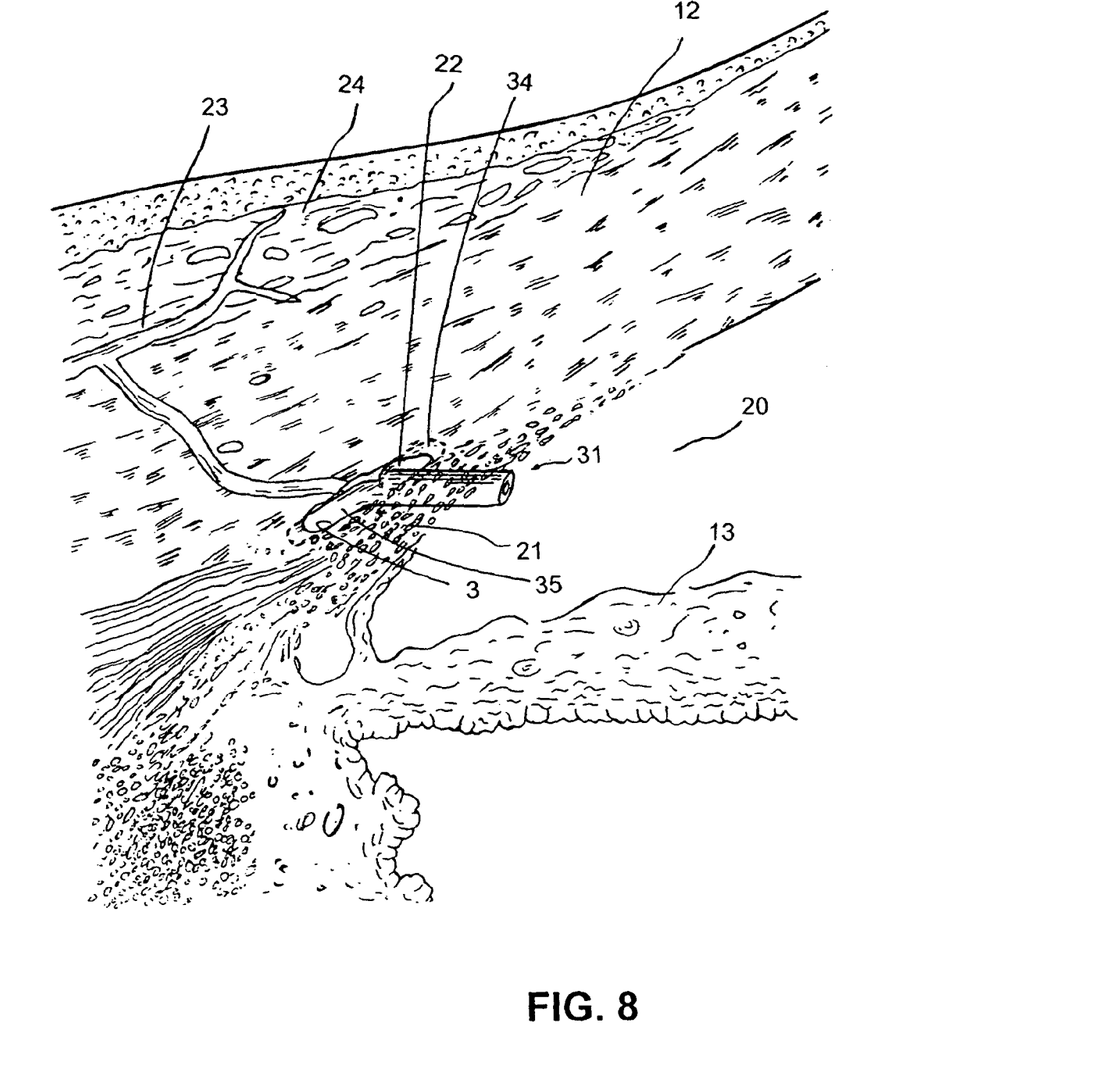
FIG. 8 is a perspective view of the trabecular shunt placed inside Schlemm's canal.

As shown in FIG. 2, the trabecular meshwork 21 is adjacent a small portion of the sclera 11. Traditional procedures that create a hole or opening for implanting a device through the tissues of the conjunctiva 24 and sclera 11 involve extensive surgery, as compared to surgery for implanting a device which ultimately resides entirely within the confines of the sclera 11 and cornea 12, as is performed in accordance with one aspect. A device 31 for establishing an outflow pathway, positioned through the trabecular meshwork 21, is illustrated in FIG. 8.

In one embodiment, a method of placing a trabecular shunt into an opening through trabecular meshwork, the method comprises advancing and positioning a trabecular shunt having two distal bifurcatable elements through the opening. In a further embodiment, a method of placing a trabecular shunt into an opening through diseased trabecular meshwork for transporting aqueous humor at the level of the trabecular meshwork and using an existing outflow pathway, the method comprises advancing and positioning a trabecular shunt having a pressure sensor for measuring the pressure of the anterior chamber of the eye through the opening. In one embodiment, the method may further comprise transmitting the measured pressure to a pressure receiver outside the body of the patient.

Figure 3A:
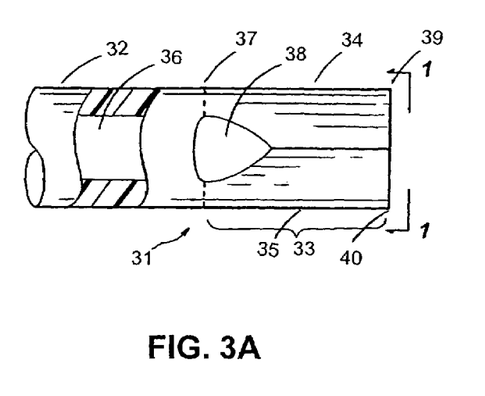
FIG. 3A is an side elevational view of a glaucoma device.

FIG. 3A shows an embodiment of the trabecular shunt 31. The trabecular shunt may comprise a biocompatible material, such as medical grade silicone, trade name Silastic(, available from Dow Corning Corporation of Midland, Mich.; or polyurethane, trade name Pellethane(, also available from Dow Corning Corporation. In some embodiments, other biocompatible materials (biomaterials) may be used, such as polyvinyl alcohol, polyvinyl pyrolidone, collagen, heparinized collagen, polytetrafluoroethylene, expanded polytetrafluoroethylene, fluorinated polymer, fluorinated elastomer, flexible fused silica, polyolefin, polyester, polyimide, polysilison, silicone, polyurethane, Nylon, polypropylene, hydroxyapetite, precious metal, Nitinol, stainless steel, or any mixture of these or other biocompatible materials. In a further embodiment, the trabecular shunt may comprise a composite biocompatible material, with a surface made of one or more of the above-mentioned biomaterials, and the surface is coated by a material selected from Teflon, polyimide, hydrogel, heparin, hydrophilic compound, anti-angiogenic factor, anti-proliferative factor, therapeutic drugs, and the like. Suitable anti-angiogenic or anti-proliferative factors may be selected from, for example, protamine, heparin, steroids, anti-invasive factor, retinoic acids and derivatives thereof, and paclitaxel or its analogues or derivatives thereof.

The main purpose of the trabecular shunt is for transporting aqueous humor at the level of the trabecular meshwork and partially using existing the outflow pathway for aqueous humor, i.e., utilizing the entire outflow pathway except for the trabecular meshwork, which is bypassed by the trabecular shunt 31. In this manner, aqueous humor is transported into Schlemm's canal and subsequently into the aqueous collectors and the aqueous veins so that the intraocular pressure is properly maintained within a therapeutic range.

In one embodiment, the trabecular shunt 31 comprises a hollow, elongated tubular element having an inlet section 32 and an outlet section 33, wherein the outlet section 33 may comprise two bifurcatable elements 34, 35 that are adapted to be bifurcated, positioned, and stabilized inside Schlemm's canal. The hollow elongated tubular element may comprise at least one lumen 36 for transporting aqueous from the anterior chamber 20 of an eye to the Schlemm's canal 22. A "bifurcatable" segment is defined as a segment, or components thereof, that can change direction away or evert from a reference axis. The "bifurcating" operation may be achieved by mechanical forces and/or through the shape-memory property of a material.

Figure 3B:
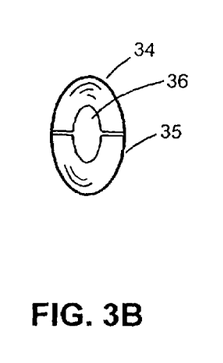
FIG. 3B is an end cross-sectional view through plane 1—1 of FIG. 3A.

For stabilization purposes, the outer surface of the outlet section 33 may comprise a stubbed surface, ribbed surface, surface with pillars, textured surface, or the like. The outer surface of the trabecular shunt 31 is biocompatible and tissue-compatible so that the interaction between the outer surface of the shunt and the surrounding tissue of Schlemm's canal is minimal, and inflammation is reduced. FIG. 3B shows an end cross-sectional view of section 1—1 of FIG. 3A. Each bifurcatable segment 34, 35 has its own end configuration. At least one of the two bifurcatable elements has a tapered distal end adapted for insertion ease. The two bifurcatable elements 34, 35 are secured to the inlet section 32 at a joint 37. In an alternate embodiment, at least a slit 38, or scalloping, within the two bifurcatable elements 34, 35 may be located near the joint 37 for stress release when the two bifurcatable elements are bifurcated in two substantially opposite directions. Other stress-releasing mechanisms may also be utilized so as to make the bifurcation operation of the bifurcatable elements safe and effective. The outlet section 33 of the trabecular shunt 31 may possess a cross-sectional shape selected from the following: oval shape, round shape, circular shape, D-shape, semi-circular shape, irregular shape, or random shape.

In another preferred embodiment, the trabecular shunt 31 may comprise a flow-restricting element for restricting at least one component in fluid, wherein the flow-restricting element may be a filter selected from a group of filtration materials comprising expanded polytetrafluoroethylene, cellulose, ceramic, glass, Nylon, plastic, and fluorinated material. Furthermore, the flow-restricting element may be a filter selected from a group of filter types comprising a hydrophobic filter, hydrophilic filter, membrane filter, microporous filter, non-woven filter, and the like. Components in blood that may be restricted by the flow-restricting element can include the following: platelet, red blood cell, white blood cell, virus, antigen, serum protein, and toxin. The flow-restricting element may also be in the form of, for example, a check valve, a slit valve, a micropump, a semi-permeable membrane, and the like. The purpose of the flow-restricting element is to keep an undesired foreign material from back flowing into the anterior chamber.

Figure 4A:
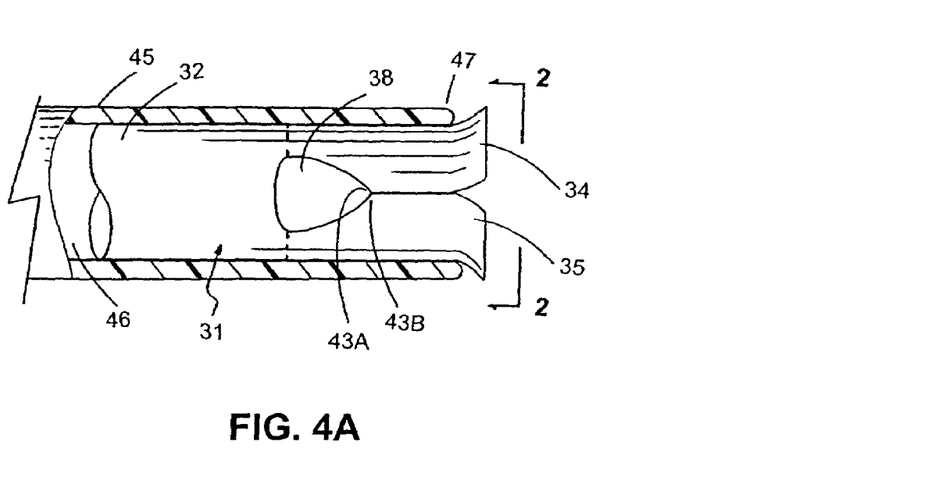
FIG. 4A illustrates the trabecular shunt of FIG. 3A at a semi-deployment state.
Figure 4B:
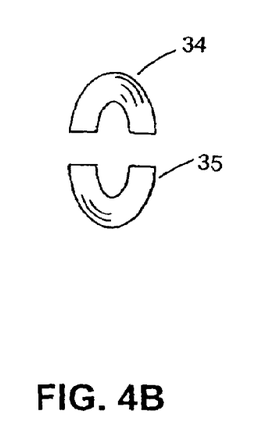
FIG. 4B is an end cross-sectional view of section 2—2 of FIG. 4A.

FIG. 4A shows the trabecular shunt of FIG. 3A in a semi-deployed state, while FIG. 4B shows an end cross-sectional view of section 2—2 of FIG. 4A. In one embodiment for shunt delivery, the trabecular shunt 31 is placed inside a hollow delivery apparatus 45. A delivery apparatus 45 comprises a distal end 47, wherein the two bifurcatable elements 34, 35 of the outlet section are self-bifurcatable in substantially two opposite directions when the trabecular shunt 31 is deployed out of the delivery apparatus 45. The slit 38 at the two bifurcatable elements 34, 35 comprises the separating regions 43A and 43B. The delivery apparatus 45 may comprise a deployment mechanism for deploying the trabecular shunt out of the delivery apparatus. In one embodiment, the deployment mechanism is a plunger. The delivery mechanism may be located at the handle of the delivery apparatus for deploying the trabecular shunt.

Figure 5A:
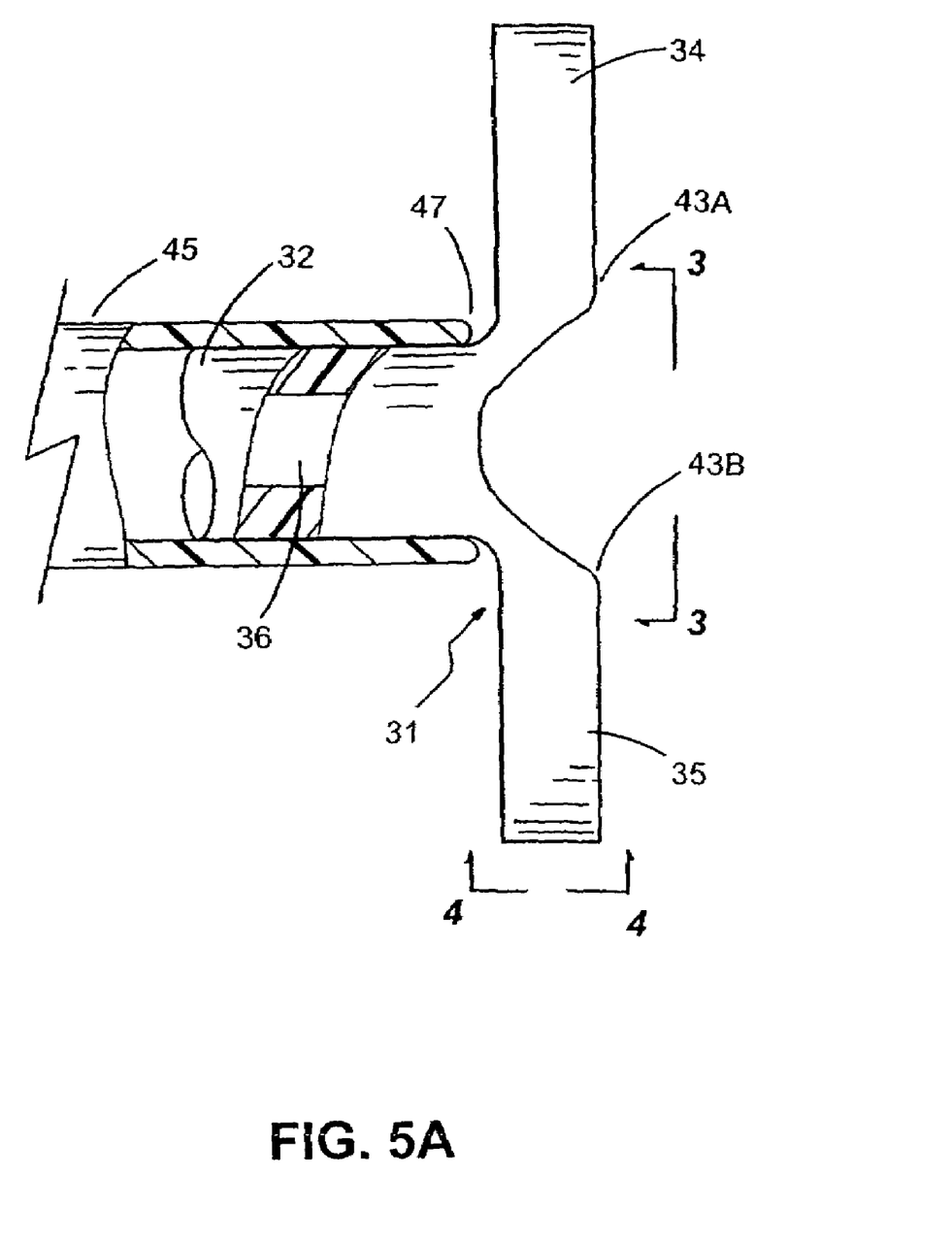
FIG. 5A illustrates the trabecular shunt of FIG. 3A in a deployed state.
Figure 7A:
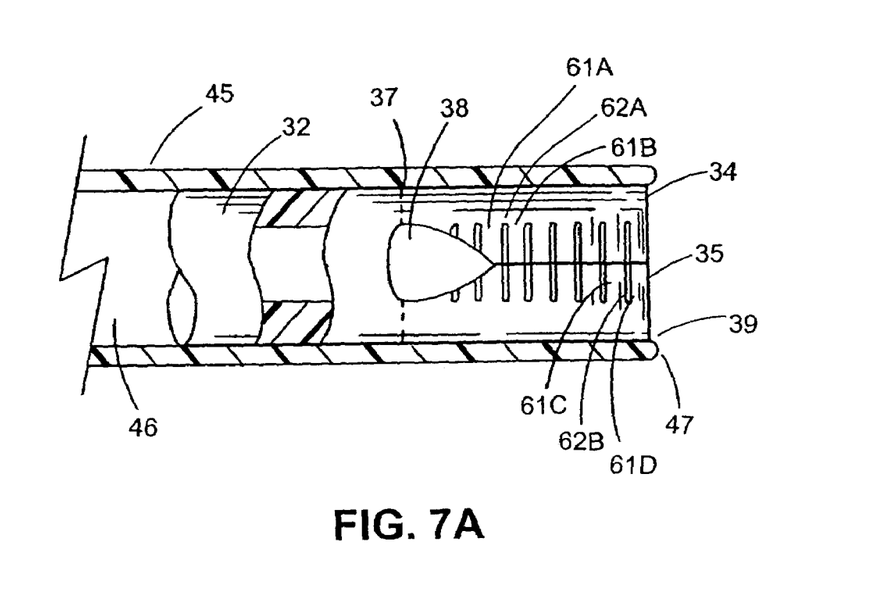
FIG. 7A is a side cross-sectional view of an alternate embodiment of the trabecular shunt.

FIG. 5A shows the trabecular shunt of FIG. 3A at a deployed state. As the plunger is continuously pushed ahead, and the distal end 47 of the delivery apparatus 45 retreats, the two bifurcatable elements 34, 35 continue to deploy in two substantially opposite directions. This may be accomplished by precontracting the two bifurcatable elements within the delivery apparatus before the delivery state. When the distal end of the delivery apparatus withdraws beyond the joint point 37 located between the inlet section 32 and the outlet section, the two bifurcatable elements are fully deployed with their separating regions 43A, 43B apart from each other. The outlet section of the preferred trabecular shunts may be made of a material form selected from a group comprising coil form, mesh form, spiral form, porous form, semi-permeable form, fishbone form (i.e., having interlocking splines and/or fenestrations in a side wall, as illustrated in FIG. 7A), continuous solid form, or may be made from any form that is effective and appropriate to evert the bifurcatable elements to be at one or more angles with respect to a reference axis of the inlet section.

Figure 5B:
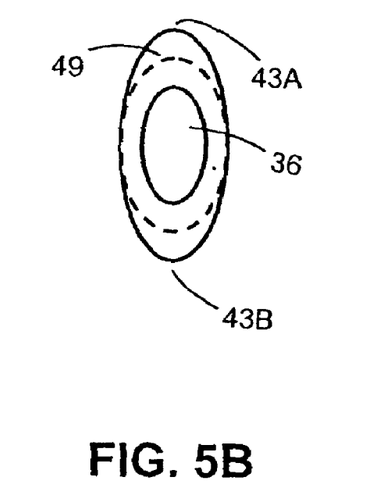
FIG. 5B is an end cross-sectional view of the trabecular shunt, section 3—3 of FIG. 5A.
Figure 5C:
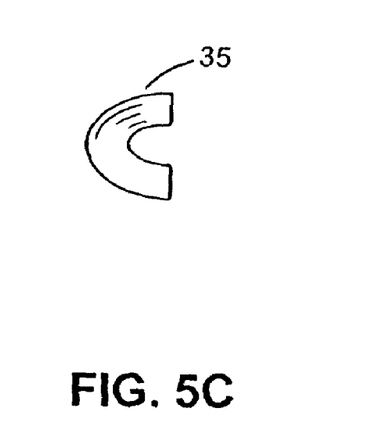
FIG. 5C is an end cross-sectional view of a bifurcatable segment, section 4—4 of FIG. 5A.

FIG. 5B shows an end cross-sectional view of the trabecular shunt, section 3—3 of FIG. 5A, while FIG. 5C shows an end cross-sectional view of a bifurcatable segment, section 4—4 of FIG. 5A. The original outer contour of the trabecular shunt 31 is illustrated by a dashed line 49 in FIG. 5B. The lumen 36 of the hollow elongated tubular element is for aqueous to flow through the trabecular shunt. The shape of the end cross-section 35 is to provide a stenting capability when the elements are placed inside Schlemm's canal. The semicircular end cross-section of the bifurcatable elements 34, 35 allows aqueous to freely flow into aqueous collector channels in the external wall of Schlemm's canal.

Figure 6:
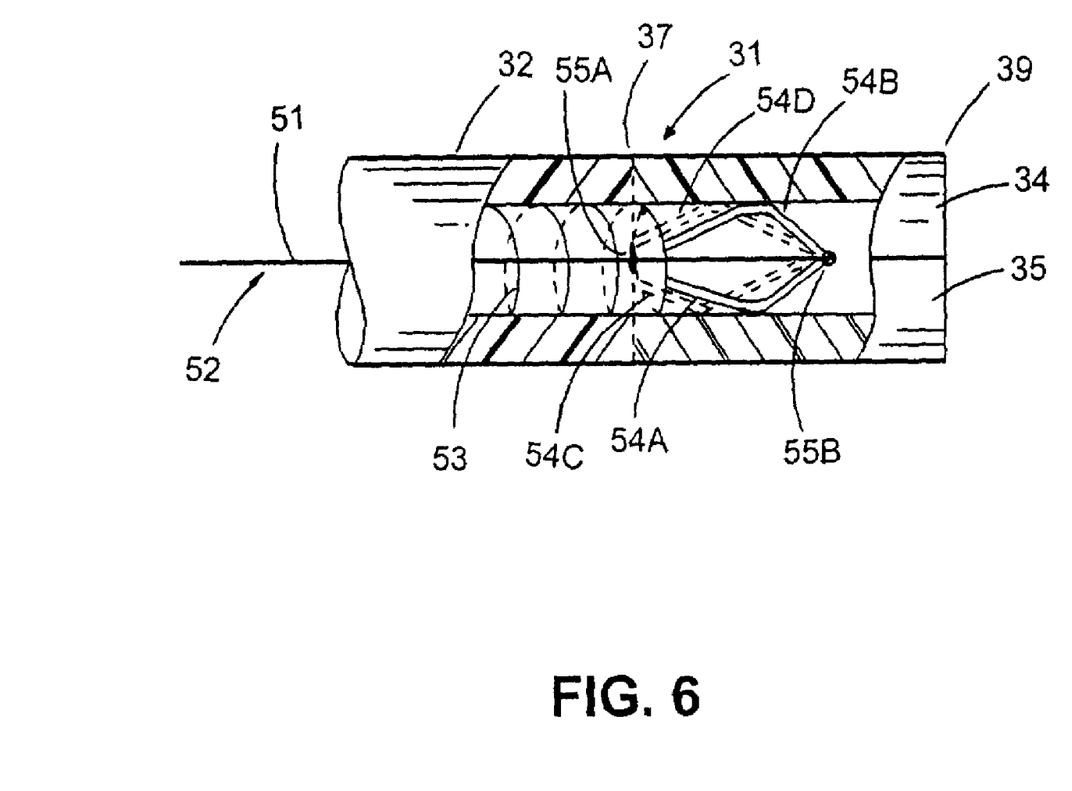
FIG. 6 is a side cross-sectional view of the trabecular shunt.

FIG. 6 shows another preferred embodiment of the trabecular shunt. A delivery applicator 52 may be placed inside a lumen of the hollow elongated tubular element, wherein the delivery applicator comprises a deployment mechanism for causing the two bifurcatable elements 34, 35 of the outlet section to move part from each other. The delivery applicator may be selected from a group consisting of a guidewire, an expandable basket, an inflatable balloon, or other expanding mechanism. In one embodiment, a delivery applicator 52 with an expandable basket comprises a plurality of expandable members 54A, 54B, 54C, 54D that all securely joined at a proximal joint 55A and at a distal joint point 55B. A distal end of a push-pull type wire 51 is also joined at the distal joint point 55B. The proximal joint 55A is located at the distal end of a compact guidewire 53 of the delivery applicator. Therefore, by pulling the push-pull wire 51 of the delivery applicator toward the operator, each of the expandable members 54A, 54B, 54C, 54D expand radially outwardly so as to effect the outward pushing action for the bifurcatable elements 34, 35.

U.S. Pat. No. 6,077,298 and U.S. patent application Ser. No. 09/452,963, filed Dec. 2, 1999, both of which are incorporated herein by reference in their entirety, disclose a medical device made of shape-memory Nitinol having a shape-transition temperature. In a further embodiment, a trabecular shunt comprises a hollow elongated tubular element having an inlet section and an outlet section, wherein the outlet section comprises two bifurcatable elements adapted to be positioned and stabilized inside Schlemm's canal. At least one of the two bifurcatable elements may be made of a shape-memory material such as shape-memory Nitinol or shape-memory plastic material. In a preferred embodiment, the shape-memory Nitinol has a preshape and a shape-transition temperature, wherein the shape-memory Nitinol bifurcates to its preshape when the shape-memory Nitinol is heated to above the shape-transition temperature, the preshape of the shape-memory Nitinol being at an angle with respect to the inlet section.

The shape-transition temperature for the shape-memory Nitinol is preferably between about 39° C. and about 90° C. The shape-transition temperature is more preferred between about 39° C. and 45° C. so as to minimize tissue damage. The angle is preferably between about 70 degrees and about 110 degrees so as to conform to the contour of Schlemm's canal. An external heat source may be provided and adapted for heating the shape-memory Nitinol to above the shape-transition temperature of the shape-memory Nitinol. Examples of such external heat sources include a heating pad, a warm cloth, a bag of warm water, remotely deliverable heat, electromagnetic field, and the like. In another embodiment, the shape-memory Nitinol may be embedded within a biocompatible material selected from, for example, silicone, polyurethane, porous material, expanded polytetrafluoroethylene, semi-permeable membrane, elastomer, and mixture of the biocompatible material thereof. In general, the bifurcatable elements are relatively flexible and soft so that they do not impart undesired force or pressure onto the surrounding tissue during and after the deployment state.

For illustration purposes, a fishbone-type outlet section is shown to render the bifurcatable elements flexible and soft during the deployment state. FIG. 7A shows an embodiment of the trabecular shunt. The trabecular shunt comprises a plurality of fishbones and their intermediate spacing, such as the fishbones 61A, 61B with a spacing 62A and the fishbones 61C, 61D with a spacing 62B. A delivery apparatus 45 may be used to deliver the self-bifurcatable elements 34, 35 having fishbones configuration.

Figure 7B:
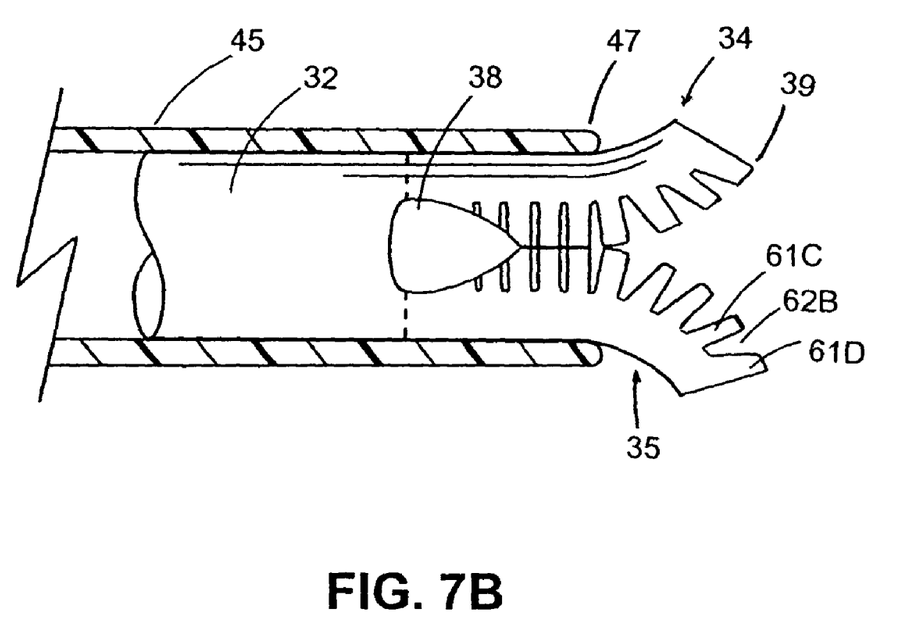
FIG. 7B is a side cross-sectional view of the trabecular shunt of FIG. 7A in a partially deployed state.

FIG. 7B shows the trabecular shunt of FIG. 7A in a semi-deployed state. As the distal end 47 of the delivery apparatus 45 is pulled away from the distal end 39 of the shunt 31, the self-bifurcatable elements 34, 35 tend to deploy to two opposite directions. In the meantime, the spacing 62B between the two fishbones 61C and 61D starts to expand and enlarge so that minimal stress is exerted on the deployed bifurcated portion of the bifurcatable elements 34, 35.

The trabecular shunt may have a length between about 0.5 mm to over a few millimeters. The outside diameter of the trabecular shunt may range from about 30 (m to about 500 (m or more. The lumen diameter is preferably in the range of about 20 (m to about 150 (m, or larger. The trabecular shunt may have a plurality of lumens to facilitate multiple-channel flow. The outlet section may be curved or angled at an angle between about 30 degrees to about 150 degrees, and preferably at about 70 degrees to about 110 degrees, with reference to the inlet section 32.

FIG. 8 is a perspective view illustrating the device 31 positioned within the tissue of an eye 10. A hole or opening is created through the diseased trabecular meshwork 21. The outlet section of the device 31 is inserted into the hole, wherein the inlet section is exposed to the anterior chamber 20 while the outlet section is positioned at about an exterior surface 3 of the diseased trabecular meshwork 21. In a further embodiment, the outlet section may enter into Schlemm's canal or other existing outflow pathways. A device as shown in FIG. 3 may be successfully used to maintain the opening through diseased trabecular meshwork.

In one embodiment, means for forming a hole/opening in the trabecular mesh 21 may comprise using a microknife, a pointed guidewire, a sharpened applicator, a screw shaped applicator, an irrigating applicator, or a barbed applicator. Alternatively, the trabecular meshwork may be dissected off with an instrument similar to a retinal pick or microcurrette. The opening may alternately be created by retrograde fiberoptic laser ablation.

In a preferred embodiment of the trabecular meshwork surgery, the patient is placed in the supine position, prepped, draped and anesthesia obtained. In one embodiment, a small (generally less than 1-mm) self-sealing incision is made. Through the cornea opposite the shunt placement site, an incision is made in the trabecular meshwork with an irrigating knife. The shunt is then advanced through the corneal incision across the anterior chamber held in a delivery apparatus or delivery applicator under gonioscopic (lens) or endoscopic guidance. The apparatus or applicator is withdrawn from the patient and the surgery is concluded. The delivery apparatus or applicator may be within a size range of 20 to 40 gauge, and preferably about 30 gauge.

In a further embodiment, a method for increasing aqueous humor outflow in an eye of a patient to reduce intraocular pressure therein, the method comprises: (a) creating an opening in trabecular meshwork using a knife or laser, etc; (b) inserting a trabecular shunt into the opening, such as by using a delivery device, wherein the trabecular shunt comprises a hollow elongated tubular element having an inlet section and an outlet section, and wherein the outlet section comprises two bifurcatable elements adapted to be positioned and stabilized inside Schlemm's canal; and (c) bifurcating the two bifurcatable elements to two opposing directions.

The method may further comprise placing the trabecular shunt inside a delivery apparatus, wherein the two bifurcatable elements are self-bifurcatable in two opposing directions when the trabecular shunt is deployed from the delivery apparatus. The method may further comprise placing a delivery applicator inside a lumen of a hollow elongated tubular element, wherein the delivery applicator comprises a deployment mechanism for causing the two bifurcatable elements to move in two opposing directions.

The method may further comprise measuring and transmitting pressure of the anterior chamber of an eye, wherein the trabecular shunt comprises a pressure sensor for measuring and transmitting pressure. The means for measuring and transmitting pressure of an anterior chamber of an eye to an external receiver may be incorporated within a device that is placed inside the anterior chamber for sensing and transmitting the intraocular pressure. Any suitable micro pressure sensor or pressure sensor chip known to those of skill in the art may be utilized.

From the foregoing description, it should be appreciated that a novel device and methods for the surgical treatment of glaucoma have been disclosed for reducing intraocular pressure. While the invention has been described with reference to specific embodiments, the description is illustrative and is not to be construed as limiting the invention. Various modifications and applications of the invention may occur to those who are skilled in the art, without departing from the true spirit or scope of the invention. The breadth and scope of the invention should be defined only in accordance with the appended claims and their equivalents.

What is claimed is:

1. A method of treating glaucoma, the method comprising:
   transporting fluid from an anterior chamber of an eye to Schlemm's canal of the eye through an implant, said implant extending between said anterior chamber and said Schlemm's canal;
   sensing an intraocular pressure using a sensor incorporated into the implant; and
   transmitting a signal indicative of the sensed pressure to an external receiver.

2. The method of claim 1, wherein the signal comprises a radiofrequency signal.

3. A method of treating glaucoma, comprising:
   providing an elongate tubular implant, said implant positioned within a delivery applicator, and said implant having an inlet section and an outlet section, wherein the outlet section comprises at least one bifurcatable element;
   inserting the delivery applicator into an eye;
   moving said implant within said delivery applicator such that said at least one bifurcatable element moves from a position that is substantially parallel to a long axis of the delivery applicator to a position that is substantially at an angle to the long axis of the delivery applicator;
   releasing said implant from said delivery applicator.

4. The method of claim 3, further comprising positioning said outlet section in Schlemm's canal of said eye.

5. The method of claim 3, further comprising positioning said at least one bifurcatable element at a collector channel of said eye.

* * * * *